(12) United States Patent
Ritchie (10) Patent No.: US 11,497,462 B2
(45) Date of Patent: Nov. 15, 2022

(54) RAPID PULSE CONFIRMATION DEVICE

(71) Applicant: WEST VIRGINIA UNIVERSITY, Morgantown, WV (US)

(72) Inventor: Michael Kyle Ritchie, Morgantown, WV (US)

(73) Assignee: WEST VIRGINIA UNIVERSITY, Morgantown, WV (US)

( * ) Notice: Subject to any disclaimer, the term of this patent is extended or adjusted under 35 U.S.C. 154(b) by 0 days.

(21) Appl. No.: 16/992,664

(22) Filed: Aug. 13, 2020

(65) Prior Publication Data

US 2021/0015446 A1    Jan. 21, 2021

Related U.S. Application Data (63) Continuation-in-part of application No. PCT/US2019/017702, filed on Feb. 12, 2019.

(Continued)

(51) Int. Cl.
*A61B 8/06* (2006.01)
*A61B 8/08* (2006.01)
(Continued)

(52) U.S. Cl.
CPC .............. *A61B 8/06* (2013.01); *A61B 8/4227* (2013.01); *A61B 8/4236* (2013.01); *A61B 8/488* (2013.01); *A61B 8/02* (2013.01)

(58) Field of Classification Search
CPC .................................................. A61B 5/681
See application file for complete search history.

(56) References Cited

U.S. PATENT DOCUMENTS 6,475,153 B1   11/2002   Khair et al.
9,775,520 B2 *  10/2017   Tran ..................... G08B 25/016
(Continued)

FOREIGN PATENT DOCUMENTS

EP   1 491 175 B1   8/2006
WO   2017032648 A1   3/2017

OTHER PUBLICATIONS

Notification of Transmittal of the International Search Report and the Written Opinion of the International Searching Authority or the Declaration dated Apr. 24, 2019 in International Application No. PCT/US2019/017702.

*Primary Examiner* — Angela M Hoffa
*Assistant Examiner* — Younhee Choi
(74) *Attorney, Agent, or Firm* — Kramer & Amado, P.C.

(57) ABSTRACT

A wearable rapid pulse confirmation (RPC) device is designed to be worn by a living subject, and includes a Doppler array comprising at least one piezoelectric ultrasonic transducer, configured to detect a change in blood velocity in a blood vessel; a screen; a loud speaker; and a band or adhesive configured to hold the wearable RPC device in proximity to a body surface of the living subject. The Doppler array is configured to detect a change in blood velocity, pulse rate, pulse strength, or a combination thereof in a blood vessel; and to provide feedback through the screen and the loudspeaker. The Doppler array may include multiple types of piezoelectric ultrasonic transducers, including low frequency piezoelectric ultrasonic transducers having a working frequency ranging from 2 MHz to <6 MHz; medium frequency piezoelectric ultrasonic transducers having a working frequency of 6 MHz to 10 MHz; and high frequency piezoelectric ultrasonic transducers having a working frequency of 10 MHz to 18 MHz.

20 Claims, 3 Drawing Sheets

Related U.S. Application Data

(60) Provisional application No. 62/629,942, filed on Feb. 13, 2018.

(51) Int. Cl.
*A61B 8/02* (2006.01)
*A61B 8/00* (2006.01)

(56) References Cited

U.S. PATENT DOCUMENTS

| | | |
|---|---|---|
| 2003/0149366 A1 | 8/2003 | Stringer et al. |
| 2008/0058623 A1* | 3/2008 | Lee .................. A61B 5/022 600/344 |
| 2010/0022886 A1 | 1/2010 | Ayati et al. |
| 2011/0071366 A1 | 3/2011 | McKenna |
| 2013/0326790 A1 | 12/2013 | Cauwels et al. |
| 2015/0039040 A1 | 2/2015 | Cowan et al. |
| 2015/0366474 A1* | 12/2015 | Pearson .............. A61B 8/06 600/495 |
| 2017/0277850 A1 | 9/2017 | Anderson |
| 2017/0340209 A1* | 11/2017 | Klaassen .............. A61B 5/11 |
| 2017/0360399 A1* | 12/2017 | Rothberg ........... B06B 1/0622 |
| 2018/0153506 A1 | 6/2018 | Rodriquez |
| 2020/0000349 A1* | 1/2020 | Lin .................. A61B 5/6841 |

* cited by examiner

RAPID PULSE CONFIRMATION DEVICE

CROSS-REFERENCE TO RELATED APPLICATIONS

This is a Continuation-In-Part of International Patent Application No. PCT/US2019/017702, filed Feb. 12, 2019, which in turn claims the benefit of U.S. Provisional Application No. 62/629,942, filed Feb. 13, 2019. The entire disclosure of each prior application is hereby incorporated by reference in its entirety.

TECHNICAL FIELD

Various embodiments disclosed herein relate generally to a rapid pulse confirmation device and, more particularly but not exclusively, to a device to determine chest compression efficacy and return of spontaneous circulation ("ROSC") during cardiopulmonary resuscitation ("CPR").

BACKGROUND

Effective chest compressions are one of the essential functions to perform for survival in CPR. Effective chest compressions are essential when delivering cardiopulmonary resuscitation (CPR) to an arresting patient. The American Heart Association (AHA) has prioritized effective chest compressions over rescue breathing, especially during out-of-hospital arrests. When providing CPR, common causes of ineffective chest compressions and thus inadequate end organ perfusion may include inexperienced rescuers, excessively long pulse check periods, insufficient force applied to the chest, low cycle rate and incomplete recoil. During the performance of CPR, a pulse check is periodically performed to assess for ROSC. The pulse check should be performed in less than 10 seconds to minimize the interruption in the delivery of chest compressions. Currently, no purpose made and portable device exists that quickly and accurately determines ROSC and that provides quantitative audio and visual feedback concerning chest compression efficacy as measured by red blood cell doppler shift velocity during CPR.

An effective chest compression, as defined by the American Heart Association, is compression of approximately ⅓ the anteroposterior diameter of the chest (i.e., approximately 2 inches in an adult or approximately 1.5 inches in an infant) at a rate of 100 cycles per minute in the adult and up to 120 cycles per minute in the neonatal population. The limitations of a depth approach are that patients are different sizes and an absolute depth is difficult to gauge during an arrest scenario. Rate is self-assessed and not actively measured leading to often low compression rates. A single rescuer often tires or the individual that is providing chest compression is often rotated every few minutes leading to great variability in the effectiveness of the compressions being provided. Furthermore, if rate and compression force are both optimized, it does not guarantee that the heart is effectively circulating blood. Extremes of body habitus, rigidity of the surface the patient is lying on, or various other factors may result in inadequate pressure applied directly to the heart leading to lack of cardiac muscle compression and thus lack of blood circulation. The device described is designed to provide near instant feedback about blood circulation during cardiac arrest.

SUMMARY

In light of the present need to create a device to improve determine ROSC in a timely manner and to evaluate chest compression efficacy, a brief summary of various exemplary embodiments is presented. Some simplifications and omissions may be made in the following summary, which is intended to highlight and introduce some aspects of the various exemplary embodiments, but not to limit the scope of the invention. Detailed descriptions of a preferred exemplary embodiment adequate to allow those of ordinary skill in the art to make and use the inventive concepts will follow in later sections.

Various embodiments disclosed herein relate to a wearable rapid pulse confirmation ("RPC") device configured to be worn by a living subject, including a Doppler array; a screen, and a loud speaker. In various embodiments, the Doppler array is configured to detect a change in blood velocity, pulse rate, pulse strength, or a combination thereof in a blood vessel; and the Doppler array is configured to provide feedback through the screen and the loudspeaker.

In various embodiments, the RPC device includes a Doppler array including an array of piezoelectric ultrasonic transducers, configured to detect a change in blood velocity in the blood vessel. The RPC device may further include at least one passive piezoelectric pressure sensor, configured to detect a change in blood velocity, pressure, or pulse rate in the blood vessel, and/or a pulse oximeter, configured to determine a ratio of oxygenated hemoglobin to deoxygenated hemoglobin in the blood vessel. The piezoelectric sensor may be included in the Doppler array of ultrasonic transducers, or the pressure sensor may be separate from the Doppler array. In various embodiments, the pulse oximeter is an infrared sensor, configured to determine a ratio of oxygenated hemoglobin to deoxygenated hemoglobin, based on a first IR absorbance value or a first IR reflectance value at about 970±30 nm and a second IR absorbance or reflectance value at about 670±30 nm.

The wearable RPC device may include a pulse oximeter an infrared spectroscopic sensor used to determine oxygenation of a target tissue, e.g., the brain, liver, or kidney. The pulse oximeter or infrared sensor includes a first infrared sensor configured to determine a ratio of oxygenated hemoglobin to deoxygenated hemoglobin, and a second infrared sensor configured to determine pulse rate. The second infrared sensor determines pulse rate based on time-dependent changes in reflection of infrared light from a tissue of a living subject. The waveform from the oximeter may be analyzed to determine wave morphology or area under the tracing curve to determine cardiac output, stroke volume, etc.

In various embodiments, the wearable RPC device further includes a band configured to hold the wearable RPC device in proximity to a body surface of a living subject, where the body surface may be a wrist, an arm, a leg, a neck, or a torso of the living subject. In various embodiments, the wearable RPC device includes a sensor configured to detect a diameter of the band after it is secured to the body portion. The wearable RPC device may further include a central processing unit configured to calculate a diameter or circumference of a body portion to which the RPC is attached, based on a change in elongation or strain of the elastic band upon attachment to the body portion. In various embodiments, the band may be used to position the wearable RPC device in proximity to an artery selected from the group consisting of a radial artery, an ulnar artery, a carotid artery, a femoral artery, and/or a combination thereof. The diameter of the band corresponds to a diameter of the body portion to which the wearable RPC device is attached. The diameter of the band may be used to estimate blood vessel depth within the body portion, and thus the amount of tissue which must be traversed by sound waves from the Doppler array to reach the blood vessel. Also, the diameter of the band may be used to estimate body composition, i.e., percentage of muscle and percentage of fat. As sound waves travel more slowly through fat than muscle, an estimation of body composition may be used to increase the accuracy of data from the Doppler array.

In various embodiments, the wearable RPC device is attached to a band with a first end and a second end, where the band includes a plurality of evenly spaced teeth on the first end, and a latch including a pawl or a tooth on the second end. The teeth on the first end engage the pawl or tooth on the second end as the first end of the band enters the latch. Once the first end of the band has entered the latch, the pawl or tooth on the second end of the band engages at least one tooth on the first end to prevent the first end of the band from being disengaged from the latch during use. The latch may include a tab or other means to disengage the pawl or tooth on the second end of the band from the teeth on the first end of the band, allowing the first end of the band to be disengaged from the latch after use to determine chest compression efficacy. The band is configured to be wrapped around a body surface, e.g., a wrist, an arm, a leg, a head, or a neck of a living subject.

In various embodiments, the wearable RPC device is attached to a band with a plurality of evenly spaced teeth on a first end, and a click counter and a latch including a pawl or a tooth on the second end. The click counter is configured to record the number of teeth which enter the latch on the second end, based on the number of teeth which pass the pawl or tooth in the second end of the band. The click counter sends a signal providing the recorded number of teeth to a CPU, which is configured to calculate a diameter or circumference of the band after insertion of the first end into the latch. The band may be used to position the wearable RPC device in proximity to a blood vessel, which may be an artery or a vein.

The wearable RPC device may include an elastic band, and a sensor configured to detect a change in elongation or strain on the band and calculate a change in band diameter based on changes in elongation or strain.

In various embodiments, the wearable RPC device further includes a hydrogel or other sonic conductive layer positioned under the Doppler array, where the hydrogel/sonic conductive layer is configured to conduct ultrasound waves from the Doppler array to a blood vessel. The hydrogel layer may be an adhesive layer configured to hold the wearable RPC device in proximity to a body surface of a living subject, the body surface being a wrist, an arm, a leg, or a neck of the living subject without the need for application of further disposable conducting liquid medium. The adhesive layer may be used in combination with a band, or instead of a band. The adhesive layer may be an adhesive polymeric hydrogel. The adhesive layer should conduct ultrasonic energy, and may be transparent to infrared light. A protective release layer may be positioned on the hydrogel layer. The release layer is removed prior to placing the hydrogel layer on a body surface.

In various embodiments, the Doppler array is configured to record a Doppler shift from moving blood vessels. The pulse oximeter is configured to determine a ratio of oxygenated hemoglobin to deoxygenated hemoglobin. A passive piezoelectric sensor may be used to determine time-dependent pressure changes in a blood vessel. An IR sensor may be used to detect reflection or refraction of blood at a tissue surface. In various embodiments, the data collected by the various sensors the wearable RPC device is sent to a CPU, is configured to calculate at least one of blood oxygenation, beats per minute, blood pressure, and relative blood velocity based on the recorded data. In various embodiments, the wearable RPC device includes a screen providing visual feedback including at least one of blood oxygenation, beats per minute, blood pressure, and relative blood velocity, based on results obtained from the CPU. The various clinical data are to be processed by the CPU to determine pulsatile flow either from ROSC or effective chest compression.

In various embodiments, the wearable RPC device includes a loudspeaker providing audible feedback regarding the efficacy of chest compressions. The loud speaker may provide audible feedback in the form of vascular sounds. Such vascular sounds may include audio feedback in the form of sound generated by blood flow. The audible feedback may be configured with a limiting mechanism, which prevents audible feedback of vascular sounds unless blood velocity or pulse rate reach a minimum threshold value. The loud speaker may provide audible feedback in the form of alarms or prerecorded messages warning that the magnitude of chest compressions is insufficient or excessive. The speaker may also give audible commands to guide CPR efforts.

In various embodiments, a wearable RPC device may include a wearable sensor, and an automated external defibrillator. The wearable sensor includes a Doppler array, and may additionally include a passive piezoelectric pressure sensor, configured to detect a change in dynamic blood pressure, blood velocity, or pulse rate in the blood vessel, and/or a pulse oximeter. A screen and a loudspeaker are provided on an automated external defibrillator. The Doppler array is configured to detect a change in blood velocity, pulse rate, pulse strength, or a combination thereof in a blood vessel; and the screen and the loudspeaker on the automated external defibrillator are configured to provide feedback based on data from the Doppler array.

Various embodiments described herein relate to an RPC device, including a Doppler array, a screen, and a loudspeaker, wherein the Doppler array detects a change in blood velocity in an artery through the Doppler array and provides feedback through the screen and the loudspeaker.

Various embodiments described herein relate to a RPC device, including an automated external defibrillator ("AED") connected to a wearable sensor, the AED device including a screen, and a loudspeaker, the AED connected to the wearable sensor, the wearable sensor including a Doppler array, wherein the Doppler array detects a change in blood velocity in an artery through the Doppler array and provides feedback through the screen and the loudspeaker.

In various embodiments, the Rapid Pulse Confirmation ("RPC") device is a wearable device designed to accurately determine chest compression efficacy and ROSC during CPR using Doppler shift measurements. The RPC device in the present embodiment may be a self-contained and stand-alone wearable device with an array of multiple Doppler piezoelectric crystals to evaluate compression efficacy and to use during a pulse check period to determine ROSC.

In an alternative embodiment, the wearable portion of the RPC device which may contain the Doppler and sensor array may be attached by a cable to an Automated External Defibrillator ("AED") that may be modified to include a power source, speaker, screen for information feedback and processor for the RPC device. The RPC device includes an array of piezoelectric crystals and/or infrared sensors which are configured to detect the Doppler shift of moving red blood cells through the radial, ulnar, carotid or femoral arteries. The Doppler array of piezoelectric crystals may be embedded into a wearable device attached to a strap for quick application to an arresting patient.

The signal from the wearable device would be routed to a CPU, which processes the signal to produce an audio or visual signal which may be provided to a loudspeaker and/or a liquid crystal display ("LCD") screen. The audio or visual signal provides produce audible and/or visual feedback to the rescuer during compressions and pulse checks. In an alternative embodiment, the signal may be routed through a central processor to apply algorithms designed for signal noise filtration and aid in determination or successful compression of ROSC. The RPC device could also be programmed with basic and advance lifesaving algorithms for guidance. The band of the wearable device would have a ratcheting device attached that would serve to track wrist, leg or neck diameter and make automatic depth adjustments needed to accurately detect a pulse. The input from the ratcheting device may be input to the central processor to make various adjustments in signal processing and Doppler function.

The sensors of the Doppler array may be organized and be configured to detect specific frequencies specified for pulse detection on the wrist, neck, head, or leg. The speaker, or a speaker in a multiple speaker set up, would be specifically tuned for reproduction of vascular tones to minimize artifact noise. The LCD screen may be fitted to the RPC device for displaying easy to read signals for compression efficacy and pulse checks, with a band, which may be an elastic or ratcheting band. The ratcheting band may automatically detect patient size, which may be used to adjust various operational parameters.

The RPC device may be a disposable, battery powered device, configured to provide clear audio and visual feedback to a user. The RPC device may be configured to measure blood velocity and/or pulse rate at the radial and ulnar arteries, but may also be designed to measure at the carotid, femoral and brachial arteries. The RPC device outputs visual and audio feedback to a user via a light bar indicator such as an LED array, a speaker, and/or a graphic display. The output visual and auditable feedback may be based on compression efficacy and pulse strength, derived from measured values of blood velocity and pulse rate.

Various embodiments disclosed herein relate to a wearable rapid pulse confirmation device configured to be worn by a living subject, including a Doppler array comprising an array of piezoelectric ultrasonic transducers, configured to detect a change in blood velocity in a blood vessel; a screen; a loudspeaker; a band configured to hold the wearable RPC device in proximity to a body surface of the living subject, said body surface being a wrist, an arm, a leg, or a neck of the living subject; and a sensor configured to detect a diameter of the band. The Doppler array may be configured to detect a change in blood velocity, pulse rate, pulse strength, or a combination thereof in a blood vessel, and to provide feedback through the screen and the loudspeaker. The array of piezoelectric ultrasonic transducers in the wearable RPC device includes:
  at least one first piezoelectric ultrasonic transducer having a first frequency,
  at least one second piezoelectric ultrasonic transducer having a second frequency which is greater than the first frequency, and
  at least one optional third piezoelectric ultrasonic transducer having a third frequency different from either the first or second frequency.

Various embodiments disclosed herein relate to a wearable rapid pulse confirmation device configured to be worn by a living subject, including a Doppler array comprising an array of piezoelectric ultrasonic transducers, configured to detect a change in blood velocity in a blood vessel; a screen; a loudspeaker; a band configured to hold the wearable RPC device in proximity to a body surface of the living subject, said body surface being a wrist, an arm, a leg, or a neck of the living subject; and a sensor configured to detect a diameter of the band;
  wherein the diameter of the band is used to adjust for blood vessel depth.

A wearable rapid pulse confirmation device is configured to be worn by a living subject, and includes:
  a Doppler array comprising an array of piezoelectric ultrasonic transducers, configured to detect a change in blood velocity in a blood vessel;
  a screen;
  a loudspeaker;
  a band configured to hold the wearable RPC device in proximity to a body surface of the living subject; and a sensor configured to detect a diameter of the band; and
  at least one of:
    a passive piezoelectric pressure sensor, configured to detect a change in blood pressure or pulse rate in the blood vessel;
    an oximeter configured to determine a ratio of oxygenated hemoglobin to deoxygenated hemoglobin based on IR absorption or IR transmission at:
      900 nm to 1,050 nm, 925 nm to 1,025 nm, or 970±30 nm, and
      600 nm to 750 nm, 625 nm to 725 nm, or 670±30 nm; and
    an infrared sensor configured to determine pulse rate based on reflection of infrared light from a tissue of the living subject.

The RPC device may be configured to be worn by a living subject, and include:
  a Doppler array comprising an array of piezoelectric ultrasonic transducers, configured to detect a change in blood velocity in the blood vessel;
  a screen, and
  a loudspeaker;
  wherein:
    the Doppler array is configured to provide feedback through the screen and the loudspeaker;
  and
    the Doppler array comprises at least two types of piezoelectric ultrasonic transducers, selected from the group consisting of:
      low frequency piezoelectric ultrasonic transducers having a working frequency ranging from 2 MHz to <6 MHz;
      medium frequency piezoelectric ultrasonic transducers having a working frequency of 6 MHz to 8 MHz; and
      high frequency piezoelectric ultrasonic transducers having a working frequency of 10 MHz to 18 MHz.

In various embodiments, the Doppler array may include the low frequency piezoelectric ultrasonic transducers, the medium frequency piezoelectric ultrasonic transducers; and the high frequency piezoelectric ultrasonic transducers in combination.

BRIEF DESCRIPTION OF THE DRAWINGS

In order to better understand various embodiments, reference is made to the accompanying drawings, wherein.

To facilitate understanding, identical reference numerals have been used to designate elements having substantially the same or similar structure or substantially the same or similar function.

DETAILED DESCRIPTION OF THE INVENTION

The description and drawings presented herein illustrate various principles. It will be appreciated that those skilled in the art will be able to devise various arrangements that, although not explicitly described or shown herein, embody these principles and are included within the scope of this disclosure. As used herein, the term, "or" refers to a non-exclusive or (i.e., and/or), unless otherwise indicated (e.g., "or else" or "or in the alternative"). Additionally, the various embodiments described herein are not necessarily mutually exclusive and may be combined to produce additional embodiments that incorporate the principles described herein.

In an attempt to satisfy AHA recommendations for more objective hemodynamic endpoints to be used during cardiac arrest, use of handheld Doppler units to quickly detect the return of spontaneous circulation during pulse checks has been proposed. However, handheld Doppler devices occupy the rescuer's hands and provide only qualitative data. Their use also requires a liquid gel medium, clinical training, and is significantly limited by motion. The rapid pulse confirmation (RPC) device described herein was designed and constructed for the dual purpose of providing feedback on blood velocity and rate of pulsation through a target artery during cardiac arrest and CPR. It was also designed to be compact, to be rapidly deployable, and to support hands-free operation once applied. The device may be designed to be positioned over a particular artery; or to be versatile in placement, allowing it to be positioned over any of multiple arteries. The RPC device can be quickly applied during a cardiac arrest, and gives meaningful feedback about the efficacy of circulation during chest compression and substantially reduces pulse check interval. The RPC device is beneficial to cardiopulmonary resuscitative efforts both in and outside the hospital, and may be of utility to first responders as a non-invasive means of assessing cardiac function.

The RPC device is able to detect the return of spontaneous circulation, with its efficacy being comparable to commonly used invasive techniques, such as use of a brachial arterial line catheter. The RPC device is able to detect a carotid pulse in cardiopulmonary bypass patients following a period of hyperkalemic arrest and resumption of spontaneous cardiac activity. The RPC device is able to detect pulsatile blood flow as quickly as a brachial artery catheter in most patients with BMI's ranging from 24.85 to 39.9. The RPC device is able to detect pulsatile blood flow in hypotensive patients with systolic pressures as low as 60 mm Hg and mean arterial pressures as low as 50 mm Hg.

The RPC device may be used to combat common errors in performing chest compressions, e.g., excessively long pulse check periods, positioning a patient on a soft surface, failure to account for variations in body habitus, application of insufficient force to the chest, low cycle rate, and incomplete recoil. The RPC can be rapidly applied to an arresting patient and provide real-time feedback to the rescuer regarding the current state of the circulatory system. The device offers rapid deployment by applying a sensor pad over an artery or vein. In some embodiments, the sensor pad is applied over a major artery, e.g., the radial, ulnar, brachial, carotid, temporal, or femoral artery, and uses a processed Doppler signal from a 2 MHz to 10 MHz piezoelectric crystal to provide feedback on red blood cell velocity, rate of pulsation during compressions, and return of pulsatile blood flow indicative of return of spontaneous circulation (ROSC) during pulse checks. In some cases, the sensor pad may be applied over an artery or vein immediately below the skin surface, e.g., the superficial temporal artery, and uses a processed Doppler signal from a 10 MHz to 16 MHz piezoelectric crystal.

When the RPC device is used on patients undergoing cardiopulmonary bypass for coronary artery bypass surgery (CABG), single heart valve replacement surgery (SHVR), or a combination of CABG/SHVR, data from the RPC device, brachial arterial line catheter, pulse oximeter, and transesophageal echocardiography (TEE) may be used during the transition from cardiopulmonary bypass support to detect return of spontaneous circulation (ROSC). This transition period provides a controlled cardiac arrest environment in human subjects with multiple invasive, gold standard monitors in place which may be compared to the RPC device performance. As seen in Table 3 below, little observed difference in time of detection of ROSC between the invasive arterial line catheter (BAC) and the non-invasive RPC device at the end of cardiopulmonary bypass was observed. As seen in Table 4 below, the secondary outcome was that there is little difference in pulse rate reading between the arterial line catheter, pulse oximeter, and the RPC device. Thus, the RPC device is a viable non-invasive alternative to invasive monitors.

A potential problem with relying on pulse oximetry or a brachial arterial line catheter to detect the return of pulsatile blood flow is that these techniques may not be reliable in the presence of a weak pulse or low cardiac output, where there may be a small difference between the systolic and diastolic blood pressure or a small time-dependent change in blood volume. In some cases where the time-dependent blood pressure change falls below a certain value, pulse oximetry and a pressure sensor in a brachial arterial line catheter may not detect pulsatile flow. Another main drawback to the brachial artery catheter is that it is invasive and requires expert skill level to position properly. Also, a pulse oximeter provides a processed signal with significant lag time. Pulse determinations with a pulse oximeter are also inaccurate at low blood pressure and/or low hemoglobin saturation levels.

Thus, where the difference between diastolic and systolic blood pressure in a patient is sufficiently high, e.g., greater than 30 mm Hg, greater than 25 mm Hg, or greater than 20 mm Hg, a computer or CPU monitoring blood pressure data from a brachial arterial line catheter is capable of detecting return of pulsatile flow. However, where the difference between diastolic and systolic blood pressure in a patient is unusually low, e.g., less than 20 mm Hg, less than 15 mm Hg, or less than 10 mm Hg, the computer or CPU monitoring blood pressure data may reject that difference as insignificant and fail to detect return of pulsatile flow. Unlike a brachial arterial line catheter, the RPC device does not depend on pressure measurements, but rather on time-dependent changes in blood velocity, as measured by a Doppler shift in the ultrasound frequency. Therefore, the RPC device is a non-invasive device capable of detecting pulsatile flow, even in cases where the time-dependent change in blood pressure is small. Ultrasonic transducers in a Doppler array also be used to generate qualitative information about changes in blood pressure. The piezoelectric ultrasonic crystals read frequency shift from reflection off of blood cells, which corresponds to a change in blood velocity. Assuming a given blood vessel diameter and resistance, changes in blood velocity may correlate to a dynamic change in blood pressure. Thus, ultrasonic data from a Doppler array may be used to obtain qualitative data about changes in blood pressure. Blood pressure may vary with resistance of a patient's blood vessel to blood flow, as well as variations in blood vessel diameter in response to a patient's medications or endogenous physiologic response. These variables are not readily predictable, so while blood velocity may correlate with blood pressure, changes in blood velocity may not produce accurate blood pressure readings.

Similarly, pulse oximetry measures changes in blood volume in the skin. As the heart beats, blood volume in the arteries changes. Since blood volume changes as a result of the pulse, pulse oximetry can detect a pulse rate. The rise in blood volume as arterial pressure increases from a diastolic value to a systolic value can be used to detect each pulse. The time interval between peak blood volume measurements corresponds to the interval between pulses, and can be used to detect pulse rate. However, this technique depends on a measurable time-dependent change in blood volume. If the difference between diastolic and systolic blood pressure in a patient is unusually low, e.g., less than 20 mm Hg, less than 15 mm Hg, or less than 10 mm Hg, pulse oximetry may not detect a significant change in blood volume in peripheral tissues, and may fail to detect return of pulsatile flow. Similarly, if cardiac output (stroke volume/pulse rate) is unusually low, pulse oximetry may not detect a significant time-dependent change in blood volume in peripheral tissues. The RPC device does not depend on changes in blood volume, but rather on time-dependent changes in blood velocity, as measured by a Doppler shift in the ultrasound frequency. Therefore, the RPC device is capable of detecting pulsatile flow, even with small changes in blood volume over time.

Transesophageal echocardiography (TEE) uses ultrasound to measure blood flow near the heart, and can be used to measure pulsatile flow. In a normal patient, TEE detects pulsatile flow with a systolic wave caused by antegrade ventricular systolic flow, with a velocity of 30-80 cm/sec, and a diastolic (D) wave caused by antegrade ventricular diastolic flow with a velocity of 20-70 cm/sec. However, TEE is an invasive procedure. A specialized probe containing an ultrasound transducer at its tip is passed into the patient's esophagus, and the procedure requires a team of highly trained medical personnel. The wearable RPC device provides a noninvasive alternative which uses ultrasound to detect pulsatile blood flow, which can be readily used by first responders, e.g., paramedics or EMS technicians, or by nurses to assess patient status. The wearable RPC device may also be used as a noninvasive alternative to TEE during medical procedures, including surgery. Finally, the wearable RPC device may be used in combination with TEE, with:

TEE being used to detect pulsatile flow near the heart, and the RPC device being used to detect pulsatile flow in peripheral tissues, e.g., the head, neck, arm, wrist, or leg.

Figure 1:
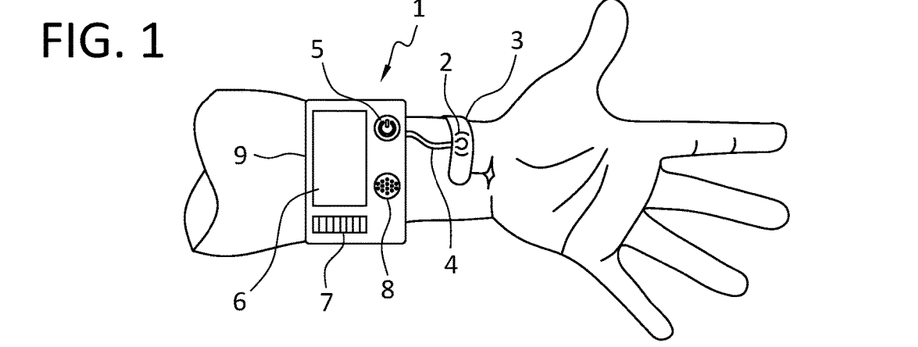
FIG. 1 illustrates a first embodiment of a wearable RPC device.

FIG. 1 illustrates a first embodiment of the wearable RPC device 1. The wearable RPC device 1 includes a housing 9 with a power button 5; a screen 6, e.g., an LCD screen; an LED array 7; and a loud speaker 8. A cable 4 connects RPC device 1 to a sensor array 2. RPC device 1 may be held to the patient's wrist by a band or strap encircling the wrist (not shown in FIG. 1). Sensor array 2 is a Doppler array, and may be held in place by a second band or strap. In various embodiments, sensor array 2 may be held in position on the wrist by an adhesive strip 3, where the adhesive strip is a hydrogel adhesive which transmits sound waves. The Doppler array contains at least one piezoelectric ultrasonic transducer, and is configured to transmit ultrasound waves at a first reference frequency $f_R$, and receive ultrasound waves at a second frequency $f_R+f_D$, where $f_D$ is the Doppler shift frequency. The frequency $f_D$ is directly proportional to blood velocity v, by the equation:

$$f_D 2 f_R v (\cos \theta)/c,$$

where θ is the angle between the path of an ultrasound beam and the path of blood flow, and c is the velocity of sound in soft tissue. The Doppler array may also be used to determine pulse rate (beats per minute, or "BPM") of a patient, or chest compression rate for a patient undergoing CPR, based on recording time-dependent changes in blood velocity, where a heart contraction or chest compression leads to an increase in blood velocity.

In various embodiments, the Doppler array may include at least one type of piezoelectric ultrasonic transducers, selected from the group consisting of:

low frequency piezoelectric ultrasonic transducers having a working frequency ranging from 2 MHz to <6 MHz;

medium frequency piezoelectric ultrasonic transducers having a working frequency of 6 MHz to 10 MHz; and high frequency piezoelectric ultrasonic transducers having a working frequency of 10 MHz to 18 MHz.

The Doppler array may include low frequency piezoelectric ultrasonic transducers, medium frequency piezoelectric ultrasonic transducers; and high frequency piezoelectric ultrasonic transducers in combination.

Low frequency transducers are able to transmit ultrasound more deeply into tissue than medium or high frequency transducers. A piezoelectric ultrasonic transducers having a working frequency ranging from 2 MHz to <6 MHz is able to transmit ultrasound to arteries and/or veins which are deep within tissue, such as the femoral artery in the leg or the carotid artery in the neck. A low frequency transducer is also able to transmit ultrasound through layers of fatty tissue to arteries or veins under the fatty layer.

Medium frequency piezoelectric ultrasonic transducers having a working frequency of 6 MHz to 10 MHz are useful for arteries or veins which are closer to the body surface, such as the radial or ulnar in the wrist, or the brachial artery in the arm.

High frequency piezoelectric ultrasonic transducers having a working frequency of 6 MHz to 10 MHz are useful for transmitting ultrasound to arteries or veins which are immediately beneath the skin, such as the superficial temporal artery in the head or the radial and ulnar arteries in patients with lower body mass indices. High frequency piezoelectric ultrasonic transducers may also be used in pediatric applications.

A Doppler array may be constructed with a single piezoelectric ultrasonic transducer, or multiple piezoelectric ultrasonic transducers having the same working frequency. If the array contains multiple piezoelectric ultrasonic transducers, they may be arranged in a hydrogel adhesive layer on a backing in a rectangular or square array, a circular array, an oval array, or a polygonal array. The piezoelectric ultrasonic transducers may be distributed randomly or non-randomly on the backing.

A Doppler array may be constructed with at least one first piezoelectric ultrasonic transducer having a first frequency, and at least one second piezoelectric ultrasonic transducer having a second frequency which is greater than the first frequency. If the array contains piezoelectric ultrasonic transducers operating at different frequencies, they may each be distributed randomly through the array. Alternatively, the first piezoelectric ultrasonic transducers may be positioned at a first part of the array, and the second first piezoelectric ultrasonic transducers may be positioned at a first part of the array. For example, a rectangular array may have the first piezoelectric ultrasonic transducers at one end of the array, and the second first piezoelectric ultrasonic transducers at the other end of the array. Alternatively, a rectangular array may have multiple rows of transducers, where the first piezoelectric ultrasonic transducers are arranged in at least two first rows, and the second first piezoelectric ultrasonic transducers are arranged in second rows, where each second row is between two first rows. In a round array, the first and second piezoelectric ultrasonic transducers may be arranged in alternating concentric rings or alternating radial rows.

In various embodiments, a piezoelectric ultrasonic transducer having a first frequency and a piezoelectric ultrasonic transducer having a second frequency may be separately activated, under the control of a processor. The selection of which transducer or transducers to be used may depend on such factors as the artery or vein to be examined, and the body mass of the patient. For example, when examining the superficial temporal artery, high frequency piezoelectric ultrasonic transducers will be selectively activated. When examining the radial or ulnar arteries in the wrist in a patient having a normal body mass index, a medium frequency piezoelectric ultrasonic transducer having a working frequency of 6 MHz to 10 MHz, or 6 to 8 MHz, may be selectively activated. When examining the radial or ulnar arteries in a patient having a high body mass index, i/e., an obese patient, a low frequency transducer having a working frequency of 2 MHz to 6 MHz may be activated.

The screen 6 in FIG. 1 may provide feedback for a person administering CPR to a patient. Such feedback may include textual or graphical data reporting instantaneous blood velocity or blood velocity as a function of time. The feedback may also provide data on pulse rate in BPM and/or a relative blood velocity meter to ensure that the rescuer is performing the CPR correctly. The screen may provide textual or graphical alerts if blood velocity or pulse rate is insufficient or too high, allowing the user to adjust the frequency and/or strength of chest compressions as needed. The loudspeaker 8 in FIG. 1 may provide audible feedback to ensure that the rescuer is performing the CPR correctly. Such feedback may include playing audio corresponding to Doppler-shifted sound waves received by the Doppler array. The loudspeaker may also provide audible alerts if blood velocity or pulse rate fall outside a defined range (too low or too high).

The LED array 7 in FIG. 1 includes a sequence of LED lights. The lights in the LED array may light up sequentially from left to right, based on data regarding one of pulse rate in BPM or blood velocity received from the CPU. The number of lights lighting up may be proportional to the value of pulse rate or blood velocity. If pulse rate or blood velocity is insufficient, no lights in the LED array may light up. Alternatively, if pulse rate or blood velocity is insufficient, a red alert light at the left end of the LED array may light up, advising a person administering CPR that more vigorous or more frequent chest compressions are required. If pulse rate or blood velocity is too high, all lights including a red alert light at the right end of the LED array may light up, advising a person administering CPR that less frequent chest compressions should be used. If pulse rate or blood velocity is too high, about 30% to about 70% of the lights in the LED array may light up, including a series of green lights in the center of the LED array 7. The audible alerts may be voice alerts or tone alerts, and are meant to guide the individual performing the chest compression to apply greater pressures, apply less pressure, increase rate, decrease rate, adjust technique or adjust patient positioning.

The RPC device of FIG. 1 may be reusable or disposable. The RPC device may be used when providing chest compressions or other life-saving treatment to a patient, e.g., during CPR. Screen 6 and or loudspeaker 8 may be used to provide alert messages if data on pulse rate or blood velocity indicates that the pulse or blood velocity is either too low or too high, allowing the user to increase the rate or depth of chest compressions. The screen 6 may provide graphical or textual reminders between CPR attempts, e.g., chest compressions, where such reminders may be administered at intervals of about 8 seconds. The screen may display textual or graphical instructions on proper CPR methods. The RPC device may detect pulse rate in terms of beats per minute ("BPM") upon the return of spontaneous circulation, and display pulse rate or blood velocity on screen 6, or using a sequence of lights in LED array 7, based on pulse/signal strength.

Figures 2, 3, 4A:
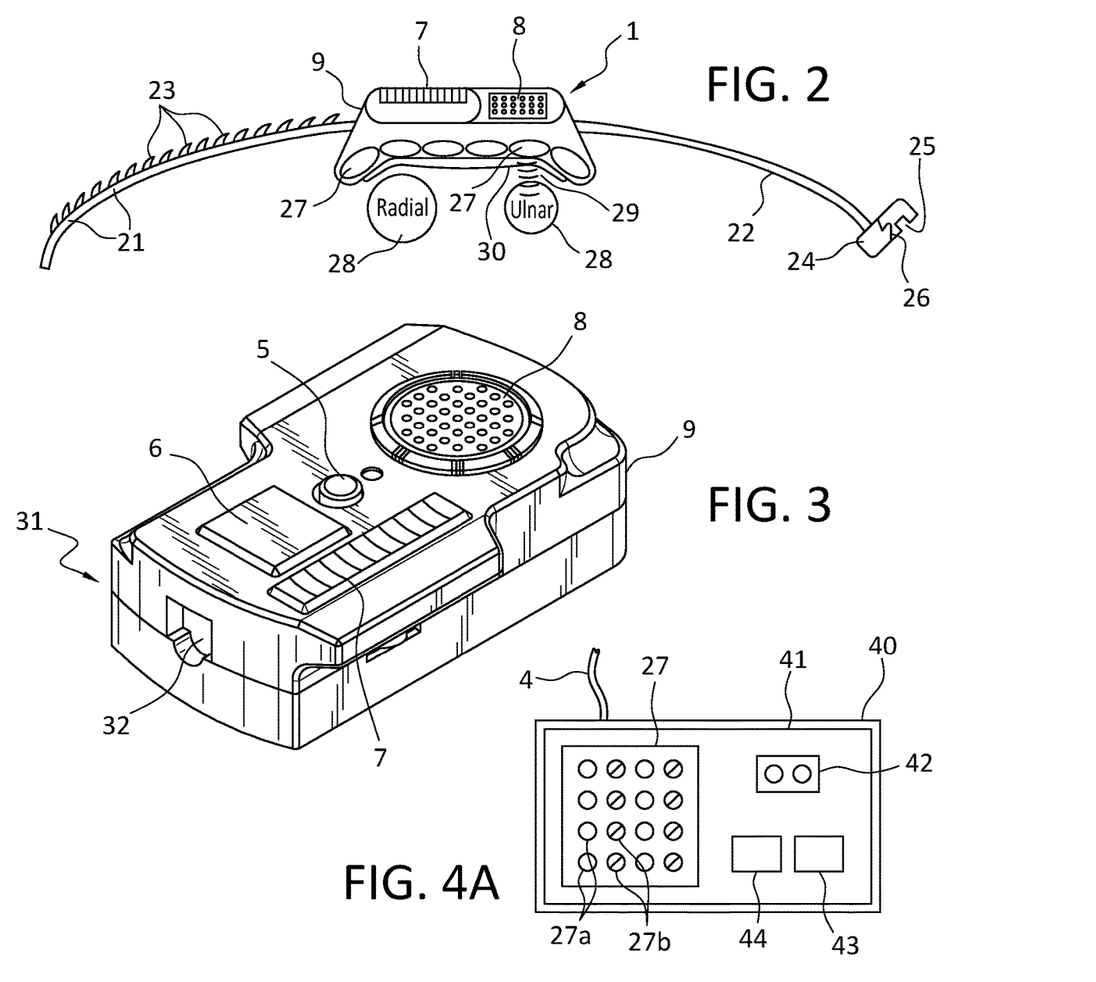
FIG. 2 illustrates a cross section view of a second embodiment of a wearable RPC device.
FIG. 3 illustrates a housing with feedback devices for use with an RPC device.
FIGS. 4A to 4F illustrate various sensor arrays for use with an RPC device.

FIG. 2 illustrates a second embodiment of the wearable RPC device 1, in which the RPC device 1 and the sensor array are incorporated into a single housing 9. The LED array 7 and/or an LCD screen (not shown in FIG. 2), together with the loudspeaker 8, are positioned on the top portion of the housing 9 of RPC device 1. The loudspeaker may receive processed signals from the CPU, and convert them into audible alerts during chest compression, or other intervention during a cardiac event. In the current embodiment, under the LED array 7 and the loud speaker 8, a Doppler array 27 is positioned on a bottom surface of housing 9. The Doppler array 27 is configured to emit continuous or pulsed ultrasonic waves 29 in the direction of a blood vessel 28. The Doppler array 27 is positioned to cover the surface of the wrist of the patient (or other surface where a pulse may be detected) and includes passive piezoelectric sensors which measure velocity of red blood cells in the target artery. Under the Doppler array 27 is a thin layer of a sound-transmitting hydrogel adhesive 30, positioned along the length of the Doppler array 27. The hydrogel adhesive layer 30 is optionally covered by a release material, such as silicone coated paper or polyester, which does not bond to the adhesive layer. When the wearable RPC device 1 is positioned on a patient, the rescuer may remove the release material to expose the adhesive layer 30 to make contact with the patient's skin, which is required for the operation of the Doppler array 27. In embodiments where a strap is used to hold RPC device 1 in position on the patient's skin, adhesive layer 30 may be replaced with a non-adhesive hydrogel. Doppler array 27 on wearable RPC device 1 is positioned in proximity to a blood vessel 28 (shown as a radial or ulnar artery in FIG. 2, although other blood vessels in the arm, leg, or neck, for example, may be used).

The wearable RPC device 1 of FIG. 2 further includes a ratcheting band having a first end 21 and a second end 22 connected to housing 9. The first end of the band 21 has a plurality of evenly spaced teeth 23, and the second end of the band 22 includes a latch 24, with an opening 25 configured to receive the first end of the wrist band 21 until the band fits a patient's wrist or other body part. A tooth or pawl 26 in latch 24 engages teeth 23 as the first end of band 21 enters latch 24, preventing accidental disengagement of the band. When strap 21 is inserted into latch 24 past pawl or tooth 26, a sensor, or click counter, detects the number of teeth 23 which pass pawl or tooth 26, as the wrist band is adjusted to fit the wrist of the patient. Information on the number of teeth 23 entering latch 24 is passed to a CPU in housing 9, which calculates the diameter and/or circumference of the wrist or other body part of the patient. This wrist band construction ensures that the wearable RPC device 1 is positioned tightly on the patient, and provides measurements to the CPU, allowing the CPU to calculate the size of the patient. The CPU may be configured to receive input from a user, providing data on age, height, and weight of the patient, as well as data identifying a body part to which the RPC device 1 is attached, e.g., wrist, leg, neck, torso, etc.

Based on data regarding the patient and the diameter of the body part, the CPU may provide an estimate as to the depth of a blood vessel 28, allowing the Doppler results to be corrected to account for the distance that sound waves 29 must travel through soft tissue to reach blood vessel 29. Also, as is known in the art, the Doppler shift frequency is directly proportional to blood velocity, and inversely proportional to the speed of sound in tissue. The speed of sound in soft tissue, e.g., muscle, is 1,540 m/s, while the speed of sound in fat is 1,450 m/s. Based on data on the size of the body part, as well as the height, weight, and age of the patient, the CPU may provide an estimate of body composition, e.g., percentage of fat in the body part. This allows an estimate of the mean velocity of sound through tissue in the body part, based on percentages of fat and soft tissue. Such an estimate of mean sound velocity may improve the accuracy of Doppler shift frequencies calculated by the CPU.

FIG. 3 illustrates a perspective view of an automated external defibrillator ("AED") device 31 for use with an alternative embodiment of the wearable RPC device including a wearable sensor. The wearable sensor may be connected to the AED device 31 using a cable, generally corresponding to cable 4 of FIG. 1, where port 32 receives the cable from the wearable sensor. The AED device may be attached to a body part with a strap, or used as a freestanding device. The AED device includes a power button 5, an LCD screen 6, an array of LED lights 7, and a loudspeaker 8, all of which function generally as described for the embodiment of FIG. 1 to provide audible and visual feedback to a person administering CPR or other lifesaving treatment. The AED device 31 may include a loud speaker 8 for providing audible feedback in the form of a Doppler tone to ensure that the rescuer is performing the CPR correctly. The AED device 31 may include a screen 6 for providing visual feedback for the rescuer, which may include feedback such as BPM and/or a relative blood velocity meter to ensure that the rescuer is performing the CPR correctly.

The wearable sensor transmits data through a cable to the AED device 31 to provide audible and visual feedback on the AED screen and speaker. Power would be supplied to the wearable sensor from the AED power supply.

FIG. 4 provides a view of a sensor array 41 which may be used with the wearable RPC device 1 of FIG. 1, where cable 4 connects the RPC device 1 to the sensor. Sensor array 41 may also be used with the AED device 31 of FIG. 3, where cable 4 connects the sensor array 41 to the port 31 on the AED device. Alternatively, the sensor may be used with the wearable RPC device 1 of FIG. 2, where sensor array 41 is positioned on the underside of housing 9, generally where Doppler array 27 is positioned in FIG. 2. When sensor array 41 is positioned on the underside of housing 9 in the embodiment of FIG. 2, cable 4 is not required to connect the sensor to the RPC device.

As shown in FIG. 4A, the sensor includes a sensor array 41 positioned on a backing 40. Sensor array 41 includes an array 27 of piezoelectric ultrasonic transmitters 27a, which transmit ultrasound waves at a first reference frequency $f_R$, and piezoelectric ultrasonic receivers 27b, which receive ultrasound waves at a Doppler-shifted frequency $f_R+f_D$, where $f_D$ is the Doppler shift frequency. In some embodiments, the array 27 may include piezoelectric ultrasonic transceivers which are configured to both transmit and receive ultrasonic waves. Data from the ultrasonic receivers 27b is transmitted to a CPU in the RPC or AED device, which calculates blood velocity from the Doppler shift frequency. The CPU may also calculate pulse rate from time-dependent changes in Doppler shift frequency. The CPU would have the ability to assess signals from the various piezoelectric crystals receiving signal and to either sum the signal or select the crystal with the strongest signal. The computer would continually make adjustments while the device is in use to account for motion artifact, device migration or other actions that may cause the need for realignment of the transducers with the target artery.

Sensor array 41 may also include one or more of the following:

a. A passive piezoelectric pressure sensor 42, applied to a body tissue above a blood vessel. Sensor 42 measures an instantaneous pressure change via a change in force applied to the sensor, where the pressure change corresponds to an increase in blood pressure. By recording instantaneous pressure change in a time-dependent manner, sensor 42 can accurately detect pulse rate in BPM. However, passive piezoelectric pressure sensors are influenced by outside movement and noise. Such sensors may not be suitable for emergency situations alone, but can be used to check accuracy of pulse rates calculated from Doppler shift data.

b. An infrared sensor 43, which measures infrared light refracted and/or reflected from a body surface to correlate to the movement of blood, where an increase in blood volume following a heartbeat or chest compression changes the reflectance of the tissue. Time-dependent changes in reflectance can be used to determine pulse rate. Since IR reflectance is a proven method for the measurement of pulse rate, but does not accurately measure the strength of the pulse, e.g., blood velocity, IR reflectance may be combined with Doppler ultrasonic data to increase measurement capabilities.

c. An infrared sensor 44 configured to measure mixed oxygen saturation of the target tissue, where the infrared sensor 44 may be:

A pulse oximeter, configured to determine a ratio of oxygenated hemoglobin to deoxygenated hemoglobin in the blood vessel, where the pulse oximeter 44 is configured to determine a ratio of oxygenated hemoglobin to deoxygenated hemoglobin, based on:
- a first IR absorbance value or a first IR reflectance value at about 970±30 nm; and
- a second IR absorbance or reflectance value at about 670±30 nm; or A near infrared oximeter, configured to determine oxygenation in deeper tissues such as the brain, liver or kidney by measuring regional oxygen saturation of the target tissue.

Sensor array 41 may be attached to a body surface of a patient with a hydrogel adhesive which conducts ultrasound and IR radiation, where the hydrogel adhesive is on backing 40. Alternatively, sensor array 41 may be attached to a body surface of a patient with a strap, and a non-adhesive hydrogel which conducts ultrasound and IR radiation may be positioned between sensor array 41 and the body surface. When the sensor array 41 is positioned on a patient, the hydrogel makes contact with the patient's skin, allowing proper propagation of ultrasonic waves and IR radiation. As provided to the user, a hydrogel layer and a protective release liner may be positioned on the sensor array. Prior to use, the release liner is removed to expose the hydrogel layer, and the sensor array is placed on the body surface through the hydrogel layer.

In various embodiments, backing 40 is a flexible backing made from a polymeric film, a woven fabric, a knitted fabric, or a non-woven textile. The flexible backing 40 is configured to be placed on a patient's body, so that the hydrogel adhesive is attached to the patient's body and the backing 40 bends or flexes to conform to the shape of the patient's body. The piezoelectric ultrasonic sensors are embedded in the hydrogel layer. The hydrogel adhesive secures the piezoelectric ultrasonic sensors in position, adjacent to the patient's skin.

Figure 4B:
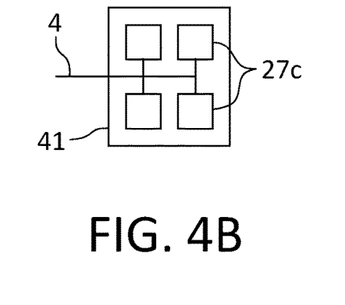

FIG. 4B shows a sensor array 41 of multiple piezoelectric ultrasonic sensors 27c, where each sensor 27c is either:
- A piezoelectric ultrasonic transceivers configured to both transmit and receive ultrasonic waves; or
- A piezoelectric ultrasonic sensor comprising a piezoelectric ultrasonic transmitter 27a and a piezoelectric ultrasonic receiver 27b.

As seen in FIG. 4B, the sensor array 41 may be a square or rectangular array, including from 2 to 20, from 2 to 10, from 2 to 4, or from 4 to 8 sensors 27a in a first direction, and from 2 to 20, from 2 to 10, from 2 to 4, or from 4 to 8 sensors 27a in a second direction normal to the first direction. Data from the ultrasonic receivers 27c is transmitted to a CPU through cable 4, which calculates blood velocity from a Doppler shift frequency, and/or pulse rate from time-dependent changes in Doppler shift frequency. Cable 4 may also transmit instructions on timing of transmission of ultrasonic pulses to the piezoelectric ultrasonic transceivers in sensors 27c from the CPU. As seen in FIG. 4B, each sensor 27c comprises a piezoelectric ultrasonic transducer having a common frequency, e.g., a working frequency of 6 MHz to 8 MHz.

Figure 4C:
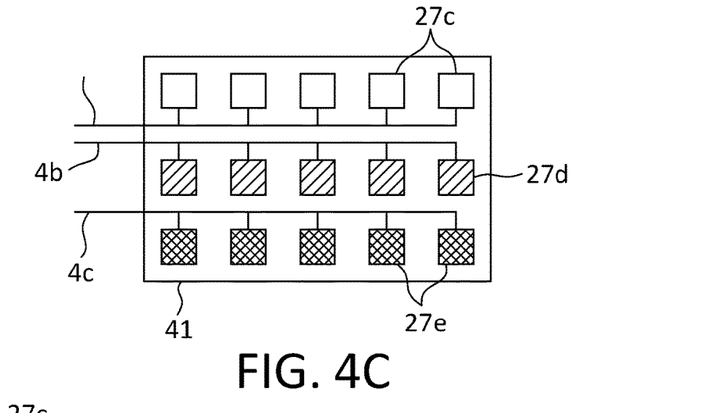

FIG. 4C shows a sensor array 41 of:
- A linear array of multiple first piezoelectric ultrasonic sensors 27c having a first working frequency, e.g., 6 to 8 MHz, which transmit and/or receive data through wire 4a;
- A linear array of multiple second piezoelectric ultrasonic sensors 27d having a second working frequency which is greater than the first frequency, e.g., 10 to 16 MHz, which transmit and/or receive data through wire 4b; and
- A linear array of multiple third piezoelectric ultrasonic sensors 27e having a third working frequency different from either the first or second frequency, e.g., 2 to <6 MHz, which transmit and/or receive data through wire 4c.

Figure 4D:
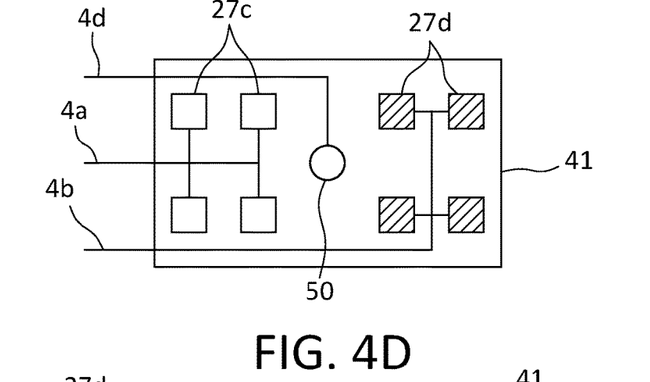

FIG. 4D shows a rectangular sensor array 41 including:
- A rectangular array of multiple first piezoelectric ultrasonic sensors 27c having a first working frequency, e.g., 6 to 8 MHz, which transmit and/or receive data through wire 4a, at a first end of the array;
- A rectangular array of multiple second piezoelectric ultrasonic sensors 27d having a second working frequency, e.g., 10 to 16 MHz, which transmit and/or receive data through wire 4b, at a second end of the array;
- A third type of sensor 50 between sensors 27c and 27d, which transmits and/or receives data through wire 4d. Sensor 50 may be:
  - a passive piezoelectric pressure sensor 42, applied to a body tissue above a blood vessel, configured to measure a change in blood pressure or a change in blood velocity;
  - an infrared sensor 43, configured to measure infrared light refracted and/or reflected from a body surface to correlate to the movement of blood;
  - an infrared sensor 44 for use as a pulse oximeter, where sensor 44 is configured to determine a ratio of oxygenated hemoglobin to deoxygenated hemoglobin; or
  - a combination thereof. The sensor may be configured to read the ratio of oxygenated and deoxygenated hemoglobin of the target artery or to provide oximeter data concerning the mixed venous saturation or of a target organ such as the brain. The mixed oximeter data from brain tissue may provide the rescuer with feedback about cerebral circulation or tissue viability.

Figure 4E:
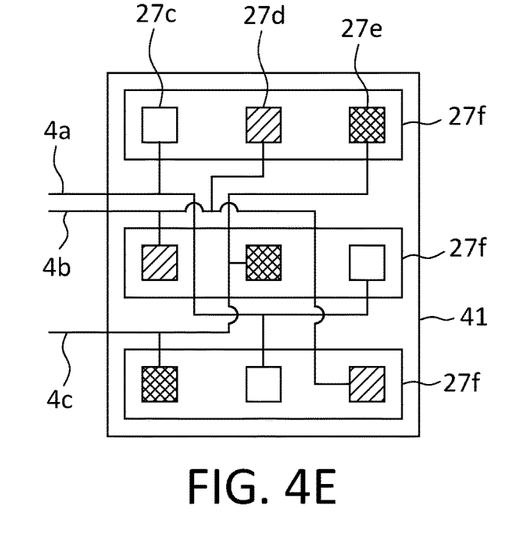

FIG. 4E shows a square or rectangular sensor array 41 containing multiple linear arrays or rows 27f of piezoelectric ultrasonic sensors, where each row 27f contains:
- At least one first piezoelectric ultrasonic sensor 27c having a first working frequency, e.g., 6 to 8 MHz, which transmits and/or receive data through wire 4a;
- At least one second piezoelectric ultrasonic sensor 27d having a second working frequency which is greater than the first frequency, e.g., 10 to 16 MHz, which transmits and/or receives data through wire 4b; and
- At least one third piezoelectric ultrasonic sensor 27e having a third working frequency different from either the first or second frequency, e.g., 2 to <6 MHz, which transmits and/or receives data through wire 4c.

Figure 4F:
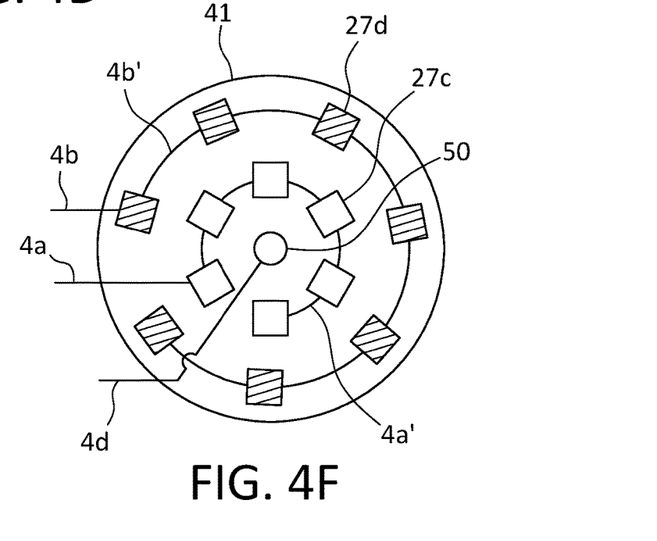

FIG. 4F shows a round sensor array 41 containing a sensor 50 at a center of array 41, which transmits and/or receives data through wire 4d. Sensor 50 may be:
- a passive piezoelectric pressure sensor 42, applied to a body tissue above a blood vessel, configured to measure a pressure change corresponding to an increase in blood pressure; an infrared sensor 43, configured to measure infrared light refracted and/or reflected from a body surface to correlate to the movement of blood;
- an infrared sensor 44 for use as a pulse oximeter, where sensor 44 is configured to determine a ratio of oxygenated hemoglobin to deoxygenated hemoglobin; or
- a combination thereof.

In various embodiments, the sensor array 41 of FIG. 4F is round, with a first circular array of first piezoelectric ultrasonic sensors 27c having a first working frequency, e.g., 6 to 8 MHz, surrounding sensor 50; and a second circular array of second piezoelectric ultrasonic sensors 27d having a second working frequency which is greater than the first frequency, e.g., 10 to 16 MHz. The first and second circular arrays may be concentric. The first circular array of sensors 27c transmits and/or receives data through wire 4a, with sensors 27c being electrically connected through wires 4a'. The second circular array of sensors 27d transmits and/or receives data through wire 4b, with sensors 27d being electrically connected through wires 4b'. In some embodiments, the sensor array 41 may be round, with:

- At least one first linear array of first piezoelectric ultrasonic sensors 27c having a first working frequency extending radially from sensor 50 toward an edge of sensor array 41; and
- At least one second linear array of second piezoelectric ultrasonic sensors 27d having a second working frequency extending radially from sensor 50 toward an edge of sensor array 41.

In various embodiments, an elliptical sensor array similar to the array of FIG. 4F may be constructed, with multiple sensors 50 being positioned on a line connecting the focal points of array 41, and at least one elliptical array of sensors 27c, 27d, and/or 27e surrounding sensors 50. In various embodiments, an elliptical sensor array similar to the array of FIG. 4F may be oval or stadium-shaped.

The piezoelectric sensors used for a given patient are selected based on such factors as vein or artery of interest, the thickness of the tissue between the skin surface to which the sensor is attached and the vein or artery, and the body mass index (BMI) of the patient.

Piezoelectric ultrasonic sensor 27d having a working frequency of 10 to 16 MHz are useful in sensors configured to be placed over the superficial temporal artery in a patient's head. The superficial temporal artery is very shallow and correlates well with intracerebral blood flow. It is advantageous as it is unaffected by rescue breathing, the presence or absence of a cervical collar, extremes of body habitus, BMI, and motion. Ultrasonic sensors 27d having a working frequency of 10 to 16 MHz may be used in combination with an infrared sensor, such as a pulse oximeter or a near infrared spectroscopy (NIRS) sensor. A pulse oximeter measures oxygen saturation within the vein or artery, e.g., the superficial temporal artery. NIRS is similar to a pulse oximeter but is used to measure regional oxygen saturation in deeper tissues beneath the vein or artery, such as brain tissue underlying the superficial temporal artery. A piezoelectric ultrasonic sensor 27d is embedded in a hydrogel layer.

In some embodiments, the sensor 27d is embedded in an adhesive hydrogel layer on a backing 61. The adhesive hydrogel layer may be placed over the superficial temporal artery in a patient's head, or other arteries which are close to the skin surface. In some embodiments, the sensor 27d is embedded in an adhesive hydrogel layer on a backing. The sensor 27d may be held in position using the adhesive hydrogel only, or by the adhesive hydrogel layer in combination with a headband. The adhesive hydrogel layer may be placed over the superficial temporal artery, or other arteries which are close to the skin surface. In some embodiments, the sensor 27d is embedded in an adhesive or non-adhesive hydrogel layer on an elastic or nonelastic band, which may be positioned on a patient's head so that the sensor 27d embedded in the hydrogel layer is positioned over the superficial temporal artery.

In some embodiments, the RPC device may contain a backing 40 with a sensor array of piezoelectric ultrasonic sensors 27c having a first working frequency, e.g., 6 to 8 MHz; and piezoelectric ultrasonic sensor 27e having a third working frequency lower than the first frequency, e.g., 2 to <6 MHz. In such embodiments, sensors 27c and 27e are embedded in an adhesive hydrogel layer on the backing 40. The backing 40 may be configured to be placed on the patient's chest, over the heart. The RPC device may then be used to obtain a noninvasive transthoracic echocardiogram (TTE), which uses high frequency soundwaves (ultrasound) to create a moving picture of the heart through the chest wall. The RPC device may then be used to detect pulsatile flow in the ventricles and/or the aortic arch, allowing detection of pulsatile blood flow at or near the heart.

Multiple RPC sensors may be used in combination. For example, a first RPC sensor array containing sensors 27c and 27e may be placed on the patient's chest, over the heart. A second RPC sensor array containing sensors 27d, with a working frequency of 10 MHz to 16 MHz, may be placed over the patient's superficial temporal artery. A third RPC sensor array may be placed on the patient's arm, wrist or leg. Once pulsatile blood flow at or near the heart is confirmed with the first RPC sensor array, data from the second and third RPC sensor arrays may be used to confirm pulsatile flow to the brain through the temporal artery and/or to the extremities, i.e., the arms or legs. Furthermore, if a sensor is placed proximal in the circulation and another distal, the time interval in the detection of maximal flow velocity may be calculated to provide information about cardiac output (CO) or systemic vascular resistance (SVR).

Returning to FIG. 2, a Doppler array 27 is positioned on a bottom surface of housing 9. The Doppler array 27 is configured to emit continuous or pulsed ultrasonic waves 29 in the direction of a blood vessel 28 in a patient's wrist, e.g., the radial or ulnar artery. Array 27 may contain piezoelectric ultrasonic sensors 27d having a working frequency of 10 to 16 MHz and piezoelectric ultrasonic sensor 27c having a working frequency of 6 to 8 MHz. In various embodiments, a CPU may cause sensors 27c and 27d to transmit ultrasound at their respective working frequencies, and record Doppler-shifted time-dependent ultrasound from blood vessel 28. In some cases, ultrasound from high frequency sensors 27d may not penetrate deeply enough into a patient's tissue to reach the blood vessel, in which case Doppler-shifted ultrasound may not be received. In such cases, the CPU may cease ultrasound transmission from sensors 27d, and rely on Doppler-shifted ultrasound received from sensors 27c. In other cases where the arteries in the wrist are close to the tissue surface, high frequency sensors 27d may provide high quality Doppler-shifted ultrasound data. In such cases, the CPU may cease ultrasound transmission from sensors 27c, and rely on Doppler-shifted ultrasound received from sensors 27d.

Alternatively, use of one of sensors 27c and 27d may be selected by the CPU, based on data about the patient. As discussed above, the device of FIG. 2 is held in position with a wrist band, and includes sensors to calculate the diameter and/or circumference of the wrist of the patient. The BMI of the patient may be calculated from the height and weight of the patient, and combined with data on the wrist circumference or diameter, may be used to calculate the probable thickness of a layer of fatty tissue overlying the radial or ulnar artery. In the presence of a thick layer of fatty tissue, ultrasound from high frequency sensors 27d may not penetrate the tissue deeply enough to reach artery 28, and will not produce high quality Doppler-shifted ultrasound data. In such cases, the CPU will rely on data from lower frequency sensors 27c. In the presence of a thin layer of fatty tissue overlying the radial or ulnar artery, ultrasound from lower frequency sensors 27c may penetrate the tissue too deeply, and may not produce high quality Doppler-shifted ultrasound data from blood in artery 28. In such cases, the CPU may rely on data from higher frequency sensors 27c.

Similar considerations apply to measurement of Doppler shift frequencies in blood vessels from larger body parts, such as the carotid artery in the neck, the brachial artery in the upper arm, or the femoral artery in the thigh. Arrays 27 useful for such arteries may contain piezoelectric ultrasonic sensors 27e having a working frequency of 2 to <6 MHz and piezoelectric ultrasonic sensor 27c having a working frequency of 6 to 8 MHz. Where the array is specifically designed for use with arteries in the upper arm, leg, or neck, the major veins may be too deep to allow proper tissue penetration by high frequency sensors 27d, and sensors 27d may not be useful.

Where a single sensor array which may be used on the superficial temporal artery, the arteries in the wrist, or arteries in the upper arm or thigh, an array containing high frequency piezoelectric ultrasonic sensors 27d, medium frequency piezoelectric ultrasonic sensors 27c, and low frequency piezoelectric ultrasonic sensors 27e, as seen in FIGS. 4C and 4E, may be used. Based on the site at which the array is applied, the target blood vessel, and the BMI of the patient, the CPU may select the sensors which are most likely to transmit ultrasound to the desired tissue depth, and selectively instruct those sensors to transmit ultrasound into the tissue of interest.

Figure 5:
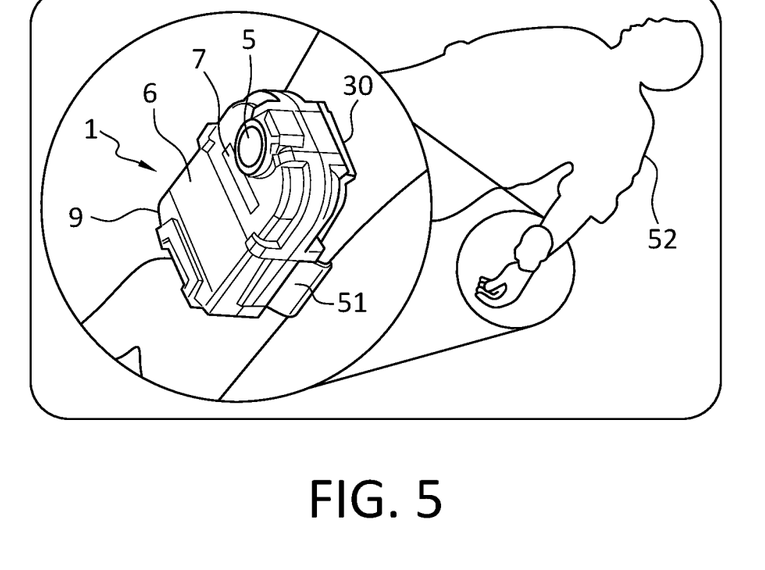
FIG. 5 illustrates a third embodiment of a wearable RPC device, positioned on the wrist of a patient.

FIG. 5 shows an alternative embodiment of the wearable RPC device 1 of FIG. 2, in which the RPC device 1 and a sensor array (not shown in FIG. 5) are incorporated into a single housing 9. A power button 5, an LED array 7, and/or an LCD screen 6 are positioned on the top portion of the housing 9 of RPC device 1. A loudspeaker, not shown in FIG. 5, may be positioned on a side or bottom surface of housing 9. Strap 51 holds the wearable RPC device on a wrist of patient 52. In the embodiment of FIG. 5, an adhesive or non-adhesive hydrogel layer 30 which conducts ultrasound and IR is positioned between a lower surface of housing 9 and the wrist of patient 52. A sensor array including at least an array of piezoelectric ultrasonic transceivers in accordance with array 27 of FIG. 2 is positioned between a bottom surface of housing 9 and the hydrogel layer 30. In various embodiments, a sensor array 41, as seen in FIG. 4, including an array 27 of piezoelectric ultrasonic transceivers in combination with a passive piezoelectric pressure sensor 42 and/or at least one IR sensor 43 or 44, may be positioned between a bottom surface of housing 9 and the hydrogel layer 30.

The RPC device 1 of FIG. 5 is capable of standalone function, with a built-in CPU. For standalone function, a graph plotting blood velocity or pulse as a function of time may be displayed on screen 6. LED array 7 may be used to provide warnings as to the presence or adequacy of pulsatile flow. Instructions on CPR or audio providing an audible signal corresponding to blood flow may be provided through a loudspeaker.

In some embodiments, the RPC device 1 may be paired with an automated external defibrillator (AED). The RPC device 1 may be wired to the AED, or connected to the AED by a near field communication wireless technology such as Bluetooth, NFC, WIFI, or 2.4/5 GHz radiowave. The AED is a portable electronic device treating cardiac arrhythmias such as ventricular fibrillation and pulseless ventricular tachycardia, and treats them through the application of electricity to stops the arrhythmia. The RPC device may be used to detect the presence or absence of pulsatile blood flow, and provide this data to the AED. If the RPC does not detect adequate pulsatile flow, the RPC device may signal the AED to initiate the application of electricity to restore adequate pulsatile flow. Once pulsatile flow is restored, the RPC device may signal the AED to cease application of electricity.

Once paired with the AED, or with a medical monitor, cell phone, or other portable electronic device, the RPC device may have additional function due to increased availability of additional CPU power, e.g., the RPC device may be configured to function using both its internal CPU and an external CPU from the paired device. An application on a cell phone or other smart device could be configured to communicate with the RPC device, so as to guide the CPR process based on data on blood flow from the RPC device.

Figure 6:
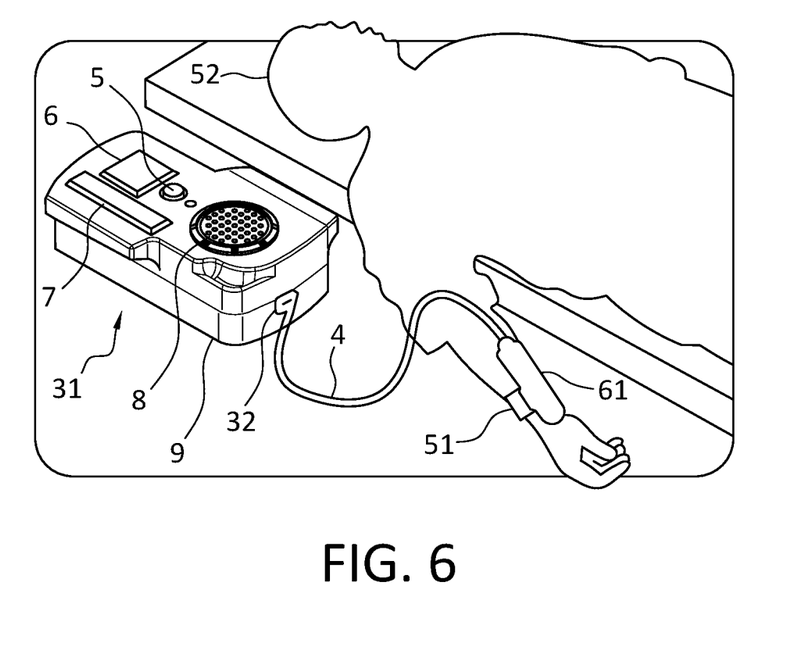
FIG. 6 illustrates a fourth embodiment of an RPC device, including an automated external defibrillator and a wrist-mounted sensor.

FIG. 6 shows a view of the embodiment of the automated external defibrillator device 31 of FIG. 3, in which the defibrillator device 31 is connected to an external sensor 61 by means of cable 4. Sensor 61 is powered by cable 4, and transmits data to a CPU in housing 9 through cable 4, which enters device 31 through port 31 in housing 9. Device 31 includes a power button 5, an LED array 7 and/or an LCD screen 6, and loudspeaker 8 on the top portion of the housing 9. Strap 51 holds the sensor 61 on a wrist of patient 52. An adhesive or non-adhesive hydrogel layer which conducts ultrasound and IR may be positioned between a sensor 61 and the wrist of patient 52. In various embodiments, sensor 61 includes a sensor array 41, as seen in FIG. 4, including an array 27 of piezoelectric ultrasonic transceivers, optionally in combination with a passive piezoelectric pressure sensor 42 and/or at least one IR sensor 43 or 44. The sensor array 41 may be positioned between a bottom surface of sensor 61 and the hydrogel layer. In various embodiments, external defibrillator device 31 may be hand-held or portable, but is not strapped to a body surface.

In an embodiment, the viability and functionality of an RPC device prototype, generally as shown in FIG. 6, may be assessed in an isolated open-heart valve or isolated coronary artery bypass graft surgery. The patients may be subjected to induction of general anesthesia, surgical exposure, initiation of cardiopulmonary bypass, and the scheduled surgical intervention.

During the process of rewarming and cessation of cardioplegia after surgery, the RPC sensor 61 may be applied to the patient's wrist, over the radial and/or ulnar arteries, over the carotid artery in the neck, over the superficial temporal artery in the head, and/or over the femoral artery in the leg. In an embodiment, the Doppler array in the RPC sensor may be positioned directly above the radial and ulnar arteries on the side opposite the peripheral arterial catheter. The anesthesia monitors may be monitored for pulsatile flow recorded by pulmonary artery and peripheral arterial catheter tracings. A Massimo pulse oximeter may also be applied to a finger on the same side of RPC device wrist application, for further confirmation of return of pulsatile flow.

The pulse rate associated with the return of pulsatile flow following cessation of cardioplegia, and the time at which pulsatile flow was detected, may be recorded based on data from arterial catheter tracings, from the pulse oximeter, and from the Doppler array in the RPC sensor. As seen in Table 3 in the Example below, detection of the return of pulsatile flow using the RPC device occurs at nearly the same time as detection of pulsatile flow with a brachial arterial catheter. Also, the pulse rate detected with the RPC device is similar to the pulse rate detected with the brachial arterial catheter.

Example: Left Carotid Artery

A study was conducted to assess the viability and functionality of an RPC device prototype. Ten patients were assessed prior to a scheduled isolated open-heart valve or isolated coronary artery bypass graft surgery. Inclusion and exclusion criteria regarding the patients are presented in Table 1.

The feasibility study was designed to assess the performance and functionality of an RPC device prototype in a controlled cardiac arrest environment. The initial device performance was evaluated by comparing its ability to detect pulsatile blood flow at a given arterial blood pressure in comparison with indwelling brachial arterial catheter tracings. Secondary data was collected for comparison of the RPC device rate and time of detection to Transesophageal echocardiography (TEE), pulse oximetry, and Electrocardiography (ECG). Patients undergoing cardiopulmonary bypass for coronary artery bypass surgery (CABG), single heart valve replacement surgery (SHVR), or a combination of CABG/SHVR were eligible for participation in this study. The patient study inclusion criteria when assessed in the pre-operative area on the morning of the scheduled cardiac surgery. The inclusion and exclusion criteria are listed in Table 1. The patient demographics are presented in Table 2.

TABLE 1

| Participation Criteria |
| --- |
| Inclusion |
| 18 years of age or older<br>Left ventricular ejection fraction (LVEF) >40% on pre-operative echocardiogram<br>Patient with single cardiac valve disease to be repaired during scheduled surgery<br>Patient undergoing coronary artery bypass<br>A combination procedure of criteria 3 and 4 |
| Exclusion |
| Redo procedure<br>Emergency procedure<br>Peripheral vascular disease<br>Previous cannulation or harvesting of radial artery<br>Arterial stents in the radial, ulnar, brachial, femoral, or carotid arteries<br>History of peripheral arterial bypass<br>History of any degree of carotid artery stenosis<br>Thoracic outlet syndrome<br>Valvular heart disease NOT being repaired the day of surgery |

TABLE 2

| Demographics | |
| --- | --- |
| Gender | |
| Male | 6 |
| Female | 4 |
| BMI (kg/m2) | |
| Mean | 31 |
| <25 | 2 |
| 25-30 | 4 |
| 31-35 | 2 |
| 36+ | 2 |

After informed consent was obtained, the patient was given pre-operative anxiolytic at the discretion of the staff anesthesiologist. The RPC probe was placed over the left carotid artery, and a baseline signal was obtained. The area was noted with a marking pen and circular double sided adhesive sticker was applied for easy identification during patient rewarming phase. The RPC probe was then removed and powered off. The patient then underwent induction of general anesthesia, surgical exposure, initiation of CPB, and the scheduled surgical intervention consistent with institutional standards.

During the process of rewarming and cessation of cardioplegia, the RPC was reapplied to the area of the carotid artery previously marked. The left carotid artery was selected due to the ease of access near the head of the bed, and its location clear from the surgical drapes and right-sided central venous catheter. After the patient had been rewarmed, the RPC device, brachial arterial catheter tracing, and the pulse oximeter were observed for the detection of pulsatile blood flow. The time of detection of the RPC device and the brachial artery catheter were recorded, as well as the arterial blood pressure at the time of detection. Of note, the values were recorded whether the patient was being supported by cardiopulmonary bypass (CPB) or if CPB had been terminated as the goal was detection of initial return of pulsatile flow, regardless of whether it was augmented by pump flow or not. Observations were made concerning the RPC device audible and visual feedback of pulsatile blood flow, as well as correlation with timing and values of other clinical monitors including ECG, transesophageal echocardiography, and pulse oximetry. Cardiopulmonary bypass pump flow was recorded if applicable. After measurements and observations were recorded, the device was removed on sternal closure and site examined for any signs of skin irritation.

The average detection time of the RPC device for pulsatile flow was within one minute of the average detection time with a brachial artery catheter ( ), with a standard deviation of 1.5 minutes. The differences in time between the brachial artery catheter detection and the RPC device detection are shown for all subjects in Table 3.

The difference in pulse rates between the RPC device, the BAC, and the pulse oximeter are shown for each patient in Table 4. Blood pressure measurements at the time of detection of Return of spontaneous circulation (ROSC) include a systolic blood pressure ranging from 60 mmHg to 90 mmHg, and a mean arterial pressure ranging from 51 mmHg to 80 mmHg. The blood pressure measured by BAC was recorded at the time when the RPC device detected return of pulsatile flow for each subject; this data is displayed in Table 5. As seen in Table 5, half of the 10 patients were hypotensive, with a BAC Mean Arterial Pressure of less then 60 mm Hg. In three patients, the pulse when pulsatile flow was detected was weak, with a difference between systolic and diastolic pressure being <15 mm Hg. In each case, the RPC device was able to detect pulsatile flow in patients with a weak pulse or hypotensive pressure.

Thus, the RPC device has demonstrated function in hypotensive patients having:
A Mean Arterial Pressure below 60 mm Hg; and/or
A systolic blood pressure below 90 mm Hg.

Specifically, as shown in Table 5, the device is able to detect pulsatile blood flow in hypotensive patients having a systolic blood pressure of 60 mm Hg to 90 mm Hg, and/or a mean arterial pressure of 51 to 80 mm Hg.

TABLE 3

Observations of the function of the RPC device versus brachial artery catheter and pulse oximeter in time of detection of pulsatile flow in minutes and beats per minute (BPM) pulse

| Subject | Time difference (minutes) | | Pulse Difference (beats per minute) |
|---|---|---|---|
| | RPC vs. BAC | Pulse Ox vs. RPC | RPC vs. BAC |
| 1 | −1 | −4 | 0 |
| 2 | 0 | −13 | −1 |
| 3 | −3 | −14 | 2 |
| 4 | −4 | −5 | 0 |
| 5 | −2 | −3 | 9 |
| 6 | 0 | −12 | −16 |
| 7 | 0 | −2 | 0 |
| 8 | 0 | 2 | 40 |
| 9 | 0 | 0 | −2 |
| 10 | 0 | −1 | 2 |

TABLE 4

Differences in pulse rate in BAC, RPC and pulse oximetry and comparisons across these devices

| Patient | Gender | BAC pulse | RPC rate | Pulse Ox (heart rate) | RPC vs. BAC pulse | RPC vs. Pulse Ox difference (BPM) |
|---|---|---|---|---|---|---|
| 1 | male | 62 | 62 | 62 | 0 | 0 |
| 2 | male | 80 | 79 | 79 | −1 | 0 |
| 3 | male | 78 | 80 | 80 | 2 | 0 |
| 4 | female | 75 | 75 | 75 | 0 | 0 |
| 5 | male | 51 | 60 | 60 | 9 | 0 |
| 6 | female | 90 | 74 | 74 | −16 | 0 |
| 7 | female | 77 | 77 | 77 | 0 | 0 |
| 8 | female | 104 | 144 | 144 | 40 | 0 |
| 9 | male | 92 | 90 | 90 | −2 | 0 |
| 10 | male | 65 | 67 | 67 | 2 | 0 |

TABLE 5

Blood pressure measurements at time of RPC detection of pulsatile flow (assessing device performance at hypotensive pressures)

| Patient | Gender | BAC Systolic Pressure (mmHg) | BAC Diastolic Pressure (mmHg) | BAC Pulse Pressure (mmHg) | BAC Mean Arterial Pressure (mmHg) |
|---|---|---|---|---|---|
| 1 | male | 62 | 48 | 14 | 52 |
| 2 | male | 84 | 37 | 47 | 52 |
| 3 | male | 90 | 63 | 27 | 72 |
| 4 | female | 75 | 39 | 36 | 51 |
| 5 | male | 87 | 65 | 22 | 72 |
| 6 | female | 89 | 76 | 13 | 80 |
| 7 | female | 74 | 67 | 7 | 69 |
| 8 | female | 60 | 53 | 7 | 55 |
| 9 | male | 88 | 74 | 14 | 78 |
| 10 | male | 69 | 51 | 18 | 57 |

As seen in Table 4, the Doppler-based measurements obtained with the RPC device provided a mean pulse rate of 80.8 beats/minute (standard deviation: 22.7 beats/minute) for the 10 patients in the study, following cessation of cardioplegia. This compares favorably with the mean pulse rate of 77.4 beats/minute (standard deviation: 14.8 beats/minute) obtained with an arterial line (BAC), and is substantially identical to the results obtained with a pulse oximeter. More importantly, Doppler measurements with the RPC device detected the return of spontaneous circulation at substantially the same time as measurements with an arterial line and by measurement with pulse oximetry, demonstrating that the Doppler-based measurements with the RPC device provide a non-invasive alternative to arterial catheters for detecting the return of blood circulation.

Although the various embodiments have been described in detail with particular reference to certain aspects thereof, it should be understood that the invention is capable of other embodiments and its details are capable of modifications in various obvious respects. As is readily apparent to those skilled in the art, variations and modifications can be effected while remaining within the spirit and scope of the invention. Accordingly, the foregoing disclosure, description, and figures are for illustrative purposes only and do not in any way limit the invention, which is defined only by the claims.

What is claimed is:

1. A wearable rapid pulse confirmation ("RPC") device configured to be worn by a living subject, comprising:
    a Doppler array, the Doppler array being configured to detect a change in at least one of blood velocity and pulse rate in a blood vessel;
    a screen,
    a speaker,
    a central processing unit (CPU),
    a band configured to hold the Doppler array in proximity to a body surface of the living subject, said body surface being a wrist, an arm, a leg, or a neck of the living subject, and
    a sensor configured to detect a diameter or circumference of the band;
    wherein the Doppler array comprises:
        at least one first piezoelectric ultrasonic transducer having a first frequency and configured to transmit a first signal to the CPU, and
        at least one second piezoelectric ultrasonic transducer having a second frequency which is greater than the first frequency, the at least one second piezoelectric ultrasonic transducer is configured to transmit a second signal to the CPU;
    wherein the CPU is configured to:
    calculate a depth of the blood vessel beneath the body surface from the diameter or circumference of the band;
    select one of the first signal and the second signal based on the blood vessel depth; and
    provide audible feedback through the speaker based on the selected signal from the Doppler array,
    wherein the audible feedback is not provided unless at least one of blood velocity and pulse rate reaches a minimum threshold value.

2. The wearable RPC device of claim 1, wherein the Doppler array further comprises at least one third piezoelectric ultrasonic transducer having a third frequency different from either the first or second frequency.

3. The wearable RPC device of claim 1, further comprising at least one passive piezoelectric pressure sensor configured to detect a change in blood pressure or pulse rate in the blood vessel.

4. The wearable RPC device of claim 1, further comprising at least one of:
    a pulse oximeter, said pulse oximeter configured to determine a ratio of oxygenated hemoglobin to deoxygenated hemoglobin based on IR absorption or IR transmission at about 970 nm and at about 670 nm; and
    an infrared sensor, said infrared sensor configured to determine pulse rate based on reflection of infrared light from a tissue of the living subject.

5. The wearable RPC device of claim 1, wherein the band has a first end and a second end, said band comprising a plurality of teeth on the first end, and a latch with a pawl or tooth on the second end,
   wherein the first end is configured to be inserted into the latch on the second end so that the teeth on the first end engage the pawl or tooth on the second end, thereby adjusting the band circumference to match the circumference of the body surface; and
   wherein the sensor is adapted to calculate said band diameter or circumference.

6. The wearable RPC device of claim 1, wherein the band is elastic.

7. The wearable RPC device of claim 1, further comprising an adhesive layer configured to hold the Doppler array in proximity to the body surface of the living subject.

8. The wearable RPC device of claim 7, wherein said adhesive layer comprises an adhesive polymeric hydrogel.

9. The wearable RPC device of claim 1, wherein the speaker is configured to provide the audible feedback comprising vascular tones based on doppler shift.

10. A system for monitoring blood velocity in a living subject, comprising:
   a wearable rapid pulse confirmation ("RPC") device configured to be worn by the living subject, comprising:
      a flexible backing, the flexible backing being configured to be mounted over a selected blood vessel in a body part of the living subject,
      a Doppler array comprising an array of piezoelectric ultrasonic transducers mounted on the flexible backing, wherein the Doppler array is configured to detect a change in blood velocity in the blood vessel and transmit a signal reporting the detected change;
      a sensor configured to detect a circumference of the flexible backing;
      a feedback device comprising a screen and/or a speaker; and
      a central processing unit (CPU),
      wherein the array of piezoelectric ultrasonic transducers comprises at least two types of piezoelectric ultrasonic transducers selected from the group consisting of:
         a first group of low frequency piezoelectric ultrasonic transducers having a working frequency ranging from 2 MHz to <6 MHz;
         a second group of medium frequency piezoelectric ultrasonic transducers having a working frequency of 6 MHz to 10 MHz; and
         a third group of high frequency piezoelectric ultrasonic transducers having a working frequency of >10 MHz to 18 MHz; and
      wherein the CPU is configured to:
         calculate a depth of the blood vessel in the body part, based on the circumference of the flexible backing,
         selectively activate one of the first group, the second group, and the third group based on the calculated depth,
         receive the signal from the Doppler array, and
         provide feedback through the feedback device based on the signal from the Doppler array.

11. The system of claim 10, wherein the array of piezoelectric ultrasonic transducers comprises the low frequency piezoelectric ultrasonic transducers, the medium frequency piezoelectric ultrasonic transducers, and the high frequency piezoelectric ultrasonic transducers.

12. The system of claim 10, wherein the CPU is configured to provide audible feedback in the form of vascular sounds through the speaker based on the signal from the Doppler array, wherein the audible feedback is not provided unless at least one of blood velocity and pulse rate reaches a minimum threshold value.

13. A system for monitoring blood velocity in a patient undergoing a cardiac event, the system comprising:
   a wearable device configured to be worn by the patient, comprising:
      a Doppler array comprising at least a first piezoelectric ultrasonic transducer having a first frequency and a second piezoelectric ultrasonic transducer having a second frequency different from the first frequency, the Doppler array being configured to transmit a first signal from the first piezoelectric ultrasonic transducer and a second signal from the second piezoelectric ultrasonic transducer;
      a band configured to hold the Doppler array in proximity to a body surface of the patient overlying a blood vessel, said body surface being a wrist, an arm, a head, a leg, or a neck of the living subject, and
      a sensor configured to transmit a third signal reporting a diameter or circumference of the band;
   a feedback device comprising a screen and/or a speaker; and
   a central processing unit (CPU) configured to receive the first and second signals from the Doppler array and the third signal from the sensor,
      wherein the CPU is configured to:
         calculate a depth of the blood vessel under the body surface from the third signal; and
         select one of the first and second signals based on the calculated depth, and calculate at least one of blood velocity and pulse rate in the blood vessel during CPR from the selected signal; and
      wherein the CPU is configured to provide feedback regarding adequacy of chest compressions and return of spontaneous circulation during CPR based on the calculated blood velocity or pulse rate,
   wherein the feedback device is configured to provide an alert through the screen or the speaker if at least one of the blood velocity and the pulse rate in the blood vessel falls outside a desired range.

14. The system of claim 13, wherein said body surface is a wrist of the living subject.

15. The system of claim 13, further comprising:
   an adhesive hydrogel layer containing the Doppler array, said hydrogel layer being configured to place the Doppler array in proximity to the body surface overlying the blood vessel and serve as a propagation medium for the ultrasonic waves.

16. The system of claim 13, wherein the screen provides visual feedback comprising at least one of beats per minute, blood pressure, and relative blood velocity.

17. The system of claim 13, wherein the blood vessel is an artery selected from the group consisting of a radial artery, an ulnar artery, a brachial artery, a temporal artery, a carotid artery, and a femoral artery.

18. The system of claim 13, wherein the CPU is configured to calculate at least one of beats per minute, blood pressure, and relative blood velocity based on the selected signal.

19. The system of claim 13, wherein the feedback device is an automated external defibrillator.

20. A system for monitoring blood velocity in a living subject, comprising:
- a wearable rapid pulse confirmation ("RPC") device configured to be worn by the living subject, comprising:
  - a flexible backing, the flexible backing being configured to be mounted on a surface of a body part over a selected blood vessel in the living subject's body, wherein the flexible backing is configured to conform to a shape of the body surface,
  - a Doppler array on the flexible backing, wherein the Doppler array is configured to detect a change in blood velocity in the blood vessel;
  - a sensor configured to detect a circumference of the flexible backing;
  - a feedback device comprising a screen and/or a speaker; and
  - a central processing unit (CPU),
  - wherein the Doppler array comprises:
    - a first low frequency piezoelectric ultrasonic transducer configured to transmit a first signal reporting the detected change; and
    - a second high frequency piezoelectric ultrasonic transducer configured to transmit a second signal reporting the detected change; and
  - wherein the CPU is configured to:
    - calculate a depth of the selected blood vessel below the surface of the body part using the circumference of the flexible backing,
    - receive the first and second signals from the Doppler array,
    - select one of the first and second signals from the Doppler array based on the calculated depth and calculate at least one of blood velocity and pulse rate in the blood vessel from the selected signal, and
    - provide audiovisual feedback through the feedback device based on the calculated blood velocity or pulse rate,
  - wherein the feedback device is configured to provide an alert through the screen or the speaker if at least one of the calculated blood velocity or pulse rate falls outside a desired range.

* * * * *